US00PP32388P2

(12) United States Plant Patent
Kleinwee

(10) Patent No.: US PP32,388 P2
(45) Date of Patent: Oct. 20, 2020

(54) *SUTERA* PLANT NAMED 'SUTZ0009'

(50) Latin Name: *Sutera cordata*
Varietal Denomination: SUTZ0009

(71) Applicant: SYNGENTA CROP PROTECTION AG, Basel (CH)

(72) Inventor: Theodorus Cornelis Maria van Kleinwee, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/602,839

(22) Filed: Dec. 10, 2019

(51) Int. Cl.
*A01H 5/02* (2018.01)
*A01H 6/00* (2018.01)

(52) U.S. Cl.
USPC ..... Plt./485

(58) Field of Classification Search
USPC ..... Plt./263.1, 485
See application file for complete search history.

*Primary Examiner* — Susan McCormick Ewoldt
*Assistant Examiner* — Karen M Redden
(74) *Attorney, Agent, or Firm* — Dale Skalla

(57) ABSTRACT

A new *Sutera* plant named 'SUTZ0009' particularly distinguished by its compact to semi trailing plant habit, good branching, large sized flowers with pink color and good floriferousness.

1 Drawing Sheet

Latin name of the genus and species of the plant claimed: *Sutera cordata.*

Varietal denomination: 'SUTZ0009'.

BACKGROUND OF THE NEW PLANT

The present invention comprises a new *Sutera*, botanically known as *Sutera cordata*, and hereinafter referred to by the variety name 'SUTZ0009'.

'SUTZ0009' is a product of a planned breeding program. The new cultivar has large sized pink colored flowers, medium to green foliage, compact to semi trailing plant habit with good branching. The new cultivar is very floriferous.

'SUTZ0009' originated from an open pollination made in the summer of 2014. The female parent is a proprietary unpatented seedling designated 'BA140073-3', having smaller and more cup shaped flower and a more trailing habit than 'SUTZ0009'. As it was an open pollination, no male parent is known.

The resultant seed was sown in a controlled breeding environment in the fall of 2014 in Enkhuizen, The Netherlands. In January 2015, 'SUTZ0009' was selected as one flowering plant within the progeny of the stated cross in Enkhuizen, The Netherlands.

The first act of asexual reproduction of 'SUTZ0009' was accomplished when vegetative cuttings were propagated from the initial selection in February 2015 in a controlled environment in Enkhuizen, The Netherlands.

BRIEF SUMMARY OF INVENTION

Horticultural examination of plants grown from cuttings of the plant initiated in February 2015, and continuing thereafter, has demonstrated that the combination of characteristics as herein disclosed for 'SUTZ0009' are firmly fixed and are retained through successive generations of asexual reproduction.

A Plant Breeder's Right for this cultivar has not yet been applied for. 'SUTZ0009' has not been made publicly available prior to the effective filing date of this application, notwithstanding any disclosure that may have been made less than one year prior to the effective filing date of this application by the inventor or another who obtained 'SUTZ0009' directly from the inventor.

'SUTZ0009' has not been observed under all possible environmental conditions. The phenotype may vary significantly with variations in environment such as temperature, light intensity and day length.

The following traits have been repeatedly observed and are determined to be basic characteristics of the new variety. The combination of these characteristics distinguishes this *Sutera* as a new and distinct variety.

DESCRIPTION OF THE PHOTOGRAPHS

Figure 1:
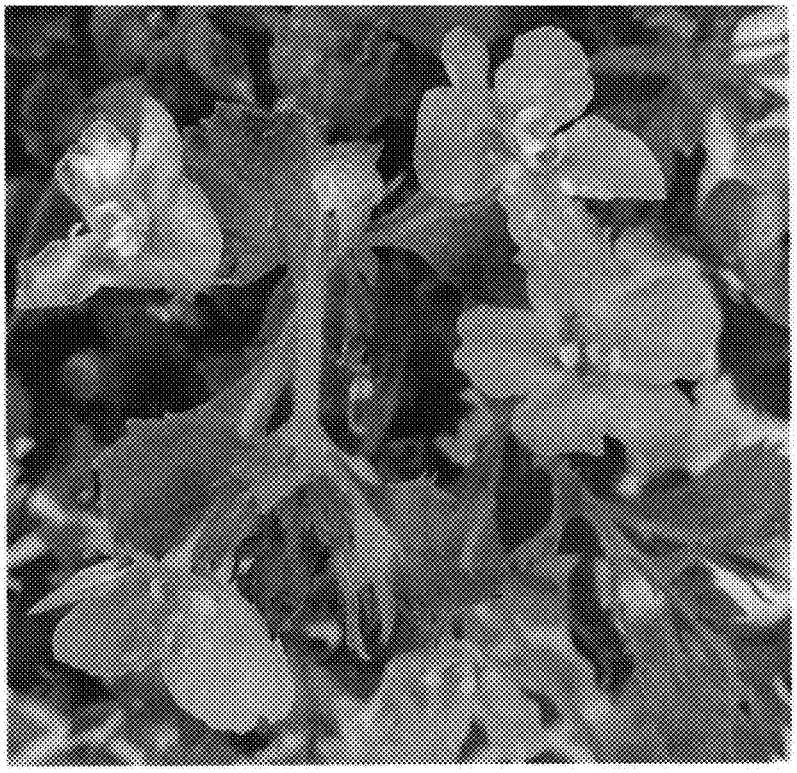
Figure 2:
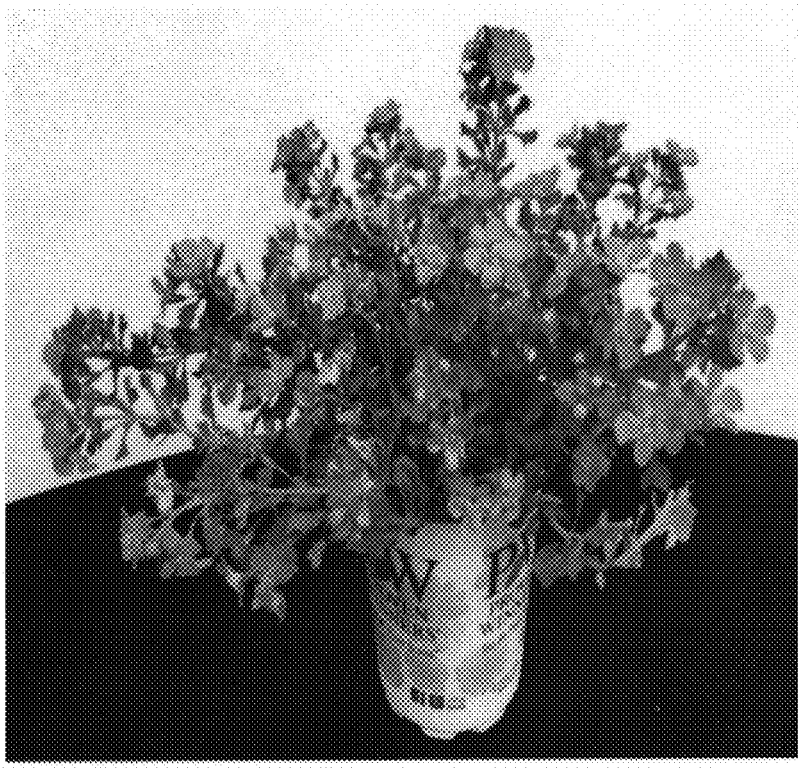

The accompanying photographic drawings show typical flower and foliage characteristics of 'SUTZ0009' with colors being as true as possible with an illustration of this type. The photograph drawing shows in FIG. 1 a close-up of the flowers, and in FIG. 2 a flowering potted plant of the new variety.

DETAILED BOTANICAL DESCRIPTION

The aforementioned photographs were taken in April 2019 from plants grown in a greenhouse trial in Gilroy, Calif. These plants were grown in 12 cm pots and were approximately 14 weeks of age. The close-up photograph was taken at the same time.

The observations and measurements were taken in Gilroy, Calif. in April 2019 on the same plants.

Color references are made to The Royal Horticultural Society Colour Chart (R.H.S.), 2001.

TABLE 1

DIFFERENCES BETWEEN THE NEW VARIETY 'SUTZ0009' AND A MOST SIMILAR VARIETY

| | 'SUTZ0009' | 'SUTZ0008' (U.S. Plant Pat. No. 29,983) |
|---|---|---|
| Flower color: | Pink | Lavender-rose |
| Flower shape: | Flat | Bit cup shaped |
| Foliage color: | Medium green | Green to dark green |

VARIETAL DENOMINATION

Plant:

*Growth and habit*.—Dense, compact to semi trailing.
*Height*.—15-17 cm.
*Spread* (*including flowers*).—38-40 cm.
*Number of branches*.—30-32.
*Time to produce a finished flowering plant*.—11-12 weeks for 12 cm pot.
*Outdoor plant performance*.—Used for hanging baskets, mixed container plantings, is very floriferous.
*Time to initiate and develop roots*.—21 days at 19-22° C.
*Root description*.—Fine, fibrous and freely branching.

Stem:

*Characteristics*.—Cross section round, high degree of self-branching.
*Stem length*.—18-25.
*Diameter*.—2-3 mm.
*Internode length*.—2.0-2.5 cm.
*Color*.—RHS 145A.
*Texture*.—Hirsute.

Foliage:

*Arrangement*.—Opposite, decussate.
*Leaf shape*.—Deltoid.
*Apex*.—Acute.
*Base*.—Attenuate.
*Margin*.—Serrate.
*Leaf length*.—Up to 2.0 cm.
*Leaf width*.—Up to 2.0 cm.
*Immature leaf, color upper surface*.—RHS 137C.
*Immature leaf, color lower surface*.—RHS 137D.
*Mature color upper surface*.—RHS 137A.
*Mature color lower surface*.—RHS 137B.
*Venation type*.—Palmate.
*Venation color*.—RHS 141C.
*Texture*.—Light pubescent on both sides; more dense pubescent on veins of lower side.

Petiole:

*Length*.—0.4 cm.
*Petiole width*.—0.3 cm.
*Petiole color*.—RHS 141C.
*Texture*.—Pubescent.

Inflorescence:

*Blooming habit*.—When temperatures don't exceed 25° C. it will bloom with many flowers through the growing season from spring to fall.
*Type of inflorescence*.—Solitary, flowers emerge from the leaf axils of the upper stem nodes, usually 2 flowers per node.
*Quantity of flowers per stem*.—3-5 flowers.
*Fragrance*.—None.

Pedicel:

*Color*.—RHS 143A.
*Length*.—1.0 cm.
*Diameter*.—0.1 cm.
*Texture*.—Densely pubescent.

Flower:

*Corolla type and shape*.—Single-type, nearly round, lower part funnel-shaped formed by 5, mainly fused petals. Upper part is salver-shaped formed by the partly free petal lobes.
*Corolla diameter*.—1.0 cm.
*Flower length*.—1.2 cm.
*Funnel diameter*.—0.3-0.4.
*Color upper surface*.—RHS 84A.
*Color lower surface*.—RHS 84B.
*Color of throat*.—RHS 17A.
*Color of funnel outer side*.—RHS 21D.

Petal (lobes):

*Apex*.—Rounded, lobed.
*Base*.—Fused.
*Margin*.—Entire.
*Texture*.—Upper side is smooth glabrous, bit puberulous in the throat. Under side glabrous to very short pubescence, increasing on the corolla tube.
*Length of lobes*, (*from the corolla opening*).—0.6 cm.
*Width of lobes*.—1.0 cm.

Flower bud:

*Shape*.—Cone-shaped.
*Diameter*.—0.4 cm.
*Length*.—0.6-0.8 cn.
*Color* (*at tight bud*).—RHS 76B at the top RHS 14C going down.

Calyx:

*Shape*.—5 sepals in a whorl around the flower base.
*Sepal shape*.—Lanceolate, fused at the base.
*Sepal color*.—RHS 143A.
*Length*.—0.5 cm.
*Width*.—About 1 mm.
*Apex*.—Acute.
*Base*.—Fused.
*Texture*.—Covered with dense hair.

Reproductive organs:

Stamens:

*Quantity*.—4.
*Filament, color*.—White, RHS 155A.
*Length*.—0.7-0.8 cm.
*Diameter*.—0.1 cm.
*Anther color*.—RHS14B.
*Pollen amount*.—Abundant.
*Pollen color*.—RHS 14B.

Pistil:

*Quantity per flower*.—One.
*Length*.—1.0 cm.
*Stigma color*.—RHS 149C.
*Style color*.—RHS 149C.

Fruit and seed set: Has not been observed to date.

Disease and insect resistance: Resistance and susceptibility typical for the species, no special observations made to date.

What is claimed is:

1. A new and distinct cultivar of *Sutera* plant named 'SUTZ0009' plant substantially as illustrated and described herein.

* * * * *